United States Patent
Ignatchenko et al.

(10) Patent No.: US 7,501,379 B2
(45) Date of Patent: Mar. 10, 2009

(54) CATALYST FOR THE PRODUCTION OF METHYL ISOPROPYL KETONE

(75) Inventors: Alexey V. Ignatchenko, Longview, TX (US); Michelle Manichanh King, Greeley, CO (US)

(73) Assignee: Eastman ChemicalCompany, Kingsport, TN (US)

( * ) Notice: Subject to any disclaimer, the term of this patent is extended or adjusted under 35 U.S.C. 154(b) by 0 days.

(21) Appl. No.: 11/525,103

(22) Filed: Sep. 22, 2006

(65) Prior Publication Data

US 2007/0088180 A1    Apr. 19, 2007

Related U.S. Application Data

(60) Provisional application No. 60/719,873, filed on Sep. 23, 2005.

(51) Int. Cl.
*B01J 23/00* (2006.01)
*B01J 20/00* (2006.01)
*B01J 21/00* (2006.01)

(52) U.S. Cl. ............. 502/351; 502/355; 502/415; 502/439

(58) Field of Classification Search ............ 502/351, 502/415, 355, 439
See application file for complete search history.

(56) References Cited

U.S. PATENT DOCUMENTS

| | | | |
|---|---|---|---|
| 2,943,081 A | 6/1960 | Howard, Jr. | |
| 3,410,909 A | 11/1968 | Fleischer et al. | |
| 3,466,334 A | 9/1969 | Young et al. | |
| 3,674,747 A * | 7/1972 | Schnegg et al. | 528/279 |
| 3,697,449 A * | 10/1972 | Brake | 564/451 |
| 3,737,492 A * | 6/1973 | Stander et al. | 264/5 |
| 4,359,410 A * | 11/1982 | Ueno et al. | 502/439 |
| 4,511,668 A * | 4/1985 | Nozue et al. | 502/84 |
| 4,950,763 A | 8/1990 | Schommer et al. | |
| 5,001,273 A | 3/1991 | Kleine-Homann | |
| 5,105,053 A | 4/1992 | Jacobson et al. | |
| 5,177,045 A * | 1/1993 | Anthony et al. | 502/164 |
| 5,180,703 A | 1/1993 | Ziebarth | |
| 5,332,433 A * | 7/1994 | Story et al. | 106/442 |
| 5,739,074 A | 4/1998 | Kocal et al. | |
| 5,849,977 A | 12/1998 | Kocal et al. | |
| 5,922,294 A | 7/1999 | Chattha | |
| 5,935,894 A | 8/1999 | Kanazirev | |
| 6,265,618 B1 | 7/2001 | Zoeller et al. | |
| 6,319,876 B1 | 11/2001 | Maier | |
| 6,369,276 B1 | 4/2002 | Warren | |
| 6,444,608 B1 | 9/2002 | Oki et al. | |
| 6,495,488 B2 | 12/2002 | Yamaguchi et al. | |
| 6,511,642 B1 | 1/2003 | Hatanaka et al. | |
| 6,517,629 B2 * | 2/2003 | Kinniard | 106/437 |
| 6,576,585 B2 | 6/2003 | Fischer et al. | |
| 6,670,303 B1 | 12/2003 | Heineke | |
| 6,677,272 B2 | 1/2004 | Beall et al. | |
| 6,797,669 B2 * | 9/2004 | Zhang et al. | 502/339 |
| 6,803,340 B2 * | 10/2004 | Lee et al. | 502/309 |
| 6,933,259 B2 * | 8/2005 | Hatanaka et al. | 502/240 |
| 7,208,446 B2 * | 4/2007 | Stamires et al. | 502/355 |
| 2002/0049137 A1 * | 4/2002 | Morikawa et al. | 502/351 |
| 2002/0150527 A1 | 10/2002 | Rossin | |
| 2007/0088181 A1 | 4/2007 | Ignatchenko et al. | |
| 2007/0093679 A1 | 4/2007 | Ignatchenko et al. | |
| 2007/0100166 A1 | 5/2007 | Beavers et al. | |
| 2007/0140952 A1 * | 6/2007 | Inoue et al. | 423/610 |
| 2007/0142682 A1 * | 6/2007 | Strebelle et al. | 570/244 |

OTHER PUBLICATIONS

Harle, V., et al., "Catalysis Assisted Characterizations of Nanosized TiO2-Al2O3 Mixtures Obtained in Molten Alkali Metal Nitrates—Effect of the Metal Precursor," Applied Catalysis A: General, vol. 196, pp. 261-269 (2000).

Abrahams, I., et al., "Lithium Ion Conductivity and Thermal Behaviour of Glasses and Crystallized Glasses in the System Li2O-Al2O3-TiO2-P2O5," Solid State Ionics, vol. 134, pp. 249-257 (2000).

* cited by examiner

*Primary Examiner*—Cam N. Nguyen
(74) *Attorney, Agent, or Firm*—William K. McGreevey; Bernard J. Graves, Jr.

(57) ABSTRACT

A catalyst for the production of methyl isopropyl ketone containing aluminum and titanium oxides, treated with Group 1 or 2 metal hydroxides, or their salts.

7 Claims, No Drawings

CATALYST FOR THE PRODUCTION OF METHYL ISOPROPYL KETONE

CROSS-REFERENCE TO RELATED APPLICATIONS

This application claims the benefit of the filing date of U.S. Provisional Patent Application No. 60/719,873, filed Sep. 23, 2005; the entire content of which is hereby incorporated by reference.

FIELD OF THE INVENTION

The present invention relates to a novel catalyst composition containing a mixture of aluminum and titanium oxides, treated with a Group 1 or 2 metal hydroxide, or a salt thereof. The catalyst composition is particularly useful for the preparation of ketones from carboxylic acids.

BACKGROUND OF THE INVENTION

Ketonization of carboxylic acids into ketones has been known for almost a century. Many metal oxides have been proposed as catalysts for the vapor-phase conversion of carboxylic acids into ketones.

Recently, U.S. Pat. No. 4,950,763 suggested using a titania catalyst for this process. According to the patent, titanium dioxide has to be used in greater than 50% by weight of the catalyst composition, apparently because of low yield.

This catalyst, however, has some disadvantages. The cost of titania is high. The titania catalyst also needs to be replaced frequently due to a short lifetime, caused by coking. Normally, the catalyst lifetime is less than 7 weeks.

Thus, there is a need in the art for a cheaper and longer lasting catalyst for the preparation of ketones from carboxylic acids.

SUMMARY OF THE INVENTION

In one aspect, the present invention relates to a catalyst for preparing ketones from carboxylic acids. The catalyst comprises a mixture of titanium dioxide and aluminum oxide, treated with a Group 1 or 2 metal hydroxide, or a salt thereof.

In another aspect, the present invention relates to a process for preparing a ketone. The process comprises the step of contacting one or more carboxylic acids with a catalyst comprising a mixture of titanium dioxide and aluminum oxide, treated with a Group 1 or 2 metal hydroxide, or a salt thereof, at conditions effective to produce a ketone.

DETAILED DESCRIPTION OF THE INVENTION

It has been surprisingly discovered that titanium dioxide mixed with aluminum oxide can be as good a catalyst for preparing methyl isopropyl ketone (MIPK) as pure titanium dioxide. By using cheap aluminum oxide in the composition with titanium oxide, the total cost of the catalyst can be significantly reduced. At the same time, the lifetime of the new catalyst can be increased.

Mixtures of aluminum oxide (alumina) and titanium dioxide (titania) may be prepared by any manner known in the art. Alumina-titania mixtures are also commercially available such as from Saint-Gobain Norpro. The catalyst can contain varying concentrations of alumina and titania. Desirable concentrations include 0.1 up to 50 weight percent of titanium dioxide, and 50 to 99.8 weight percent of aluminum oxide, based on the total weight of the catalyst composition.

The catalyst composition may include other components that do not adversely affect the reaction, such as inert material. Inert material may include materials with low surface area. The inert material can be premixed with the active catalyst material, or can be added as a mechanically separable material from the catalyst composition when it is loaded into the reactor. The inert material is not counted in the preferred range of zirconia and titania weight distribution. Thus, the catalyst composition may include silica as the major component, for example, 90% by weight, and 4% titania and 6% alumina. The active components in this case will constitute 40% titania and 60% alumina by weight according to our definition. We define the inert material as one in which its pure form does not catalyze ketonization of carboxylic acids in greater than 1-5% yield under typical conditions used in our invention.

The alumina-titania mixture can be modified with a Group 1 or 2 metal hydroxide or salt. Favorable metals include sodium, potassium, cesium, and lithium from Group 1 and calcium, strontium, barium, and magnesium from Group 2. The other members of Groups 1 and 2 can also produce ketones in the same manner, but they may generally be less effective. The more desirable of these promoters include potassium, sodium, rubidium, magnesium, calcium, strontium, and barium.

Suitable counterions of the metal salts include carbonate, oxide, carboxylate salts of mono- or poly-basic carboxylic acids containing 1-20 carbon atoms, nitrate, nitrite, or any of various organometallics which under calcining conditions oxidize to hydroxides or oxides.

Incorporating the Group 1 or 2 promoter can take place by several methods. The first is an exchange effected by soaking a solution of the exchanging agent in a suitable solvent with the solid alumina-titania mixture. The second is by incipient wetness techniques with any amount of exchanging agent. Other methods include co-precipitation of alumina-titania from a suitable precursor and the promoter simultaneously.

After incorporating the Group 1 or 2 promoter, the catalyst may be dried and/or calcined at elevated temperature. This step is optional since the catalyst will typically be heated in the reactor before it contacts any starting material. During that heating step, the catalyst is effectively dried and/or calcined.

Regardless of the incorporation method, there is a maximum amount of exchanging agent that is optimum. The production of ketones will take place at levels above or below the optimum; however, the production of ketones, especially mixed ketones, will not be optimal at these levels.

The optimum level of catalyst promoter depends on the exact agent. But with an agent such as potassium hydroxide, it will typically fall in the 0.1-20 weight percent range. More desirable levels are found in the 0.25-10 weight percent range. And the most desired loading level is 0.5-5 weight percent, based on the total weight of the catalyst composition.

Preferably, the catalyst compositions of the present invention include less than 10 percent by weight of another material that is catalytically active for ketonization, such as zirconium dioxide. More preferably, the catalyst compositions do not include other catalytically active materials.

The catalyst compositions of the present invention are particularly useful in preparing ketones from carboxylic acids. The process comprises the step of contacting at least one carboxylic acid with the catalyst compositions mentioned above at conditions effective to produce a ketone.

Carboxylic acids that can be converted to ketones using the catalysts of the present invention include those having the general formulae (Ia) and (Ib):

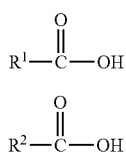

$$R^1-\underset{\underset{O}{\|}}{C}-OH \quad \text{(Ia)}$$

$$R^2-\underset{\underset{O}{\|}}{C}-OH \quad \text{(Ib)}$$

where $R^1$ and $R^2$ may be the same or different and are each independently alkyl, cycloalkyl, arylalkyl, aryl, or hetaryl.

The ketones that are produced have the general formula (II):

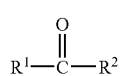

$$R^1-\underset{\underset{O}{\|}}{C}-R^2 \quad \text{(II)}$$

where $R^1$ and $R^2$ are the same as in formulae (Ia) and (Ib). If $R^1$ is identical to $R^2$, then the ketones are symmetrical. If $R^1$ is not identical to $R^2$, then the ketones are asymmetrical.

$R^1$ and $R^2$ are each preferably alkyl having 1 to 17 carbon atoms, cycloalkyl having 3 to 8 ring members, arylalkyl of 7 to 12 carbon atoms, aryl or hetaryl, and one or more of the radicals $R^1$ and $R^2$ carry one or more hydrogen atoms on the α-carbon atom.

Examples of ketones that are obtainable by the process of the present invention from the corresponding acids are diethyl ketone, di-n-propyl ketone, diisopropyl ketone, methyl propyl ketone, methyl isopropyl ketone, ethyl isopropyl ketone, nonan-5-one, octane-2,7-dione, cyclopentanone, cycloheptanone, acetophenone, propiophenone, butyrophenone, isobutyrophenone, valerophenone, phenylacetone, 1,2-diphenylacetone, cyclohexyl methyl ketone, cyclohexyl phenyl ketone, cyclopropyl methyl ketone, pinacolone and even heterocyclic ketones, such as 3-acetylpyridine, 4-acetylpyrazole and 4-acetylimidazole.

The contacting step may be carried out in any reactor known in the art.

The temperatures in the reactive zone can be in the 250-550° C. range. They can also be in the 300-500° C. range. Alternatively, they can occur in the 400-450° C. range.

The ketonization reaction can be run over a wide range of pressures. Suitable pressures include 0 to 800 psi and, particularly, 50 to 100 psi.

As used herein, feed rates refer to the quantity of condensed reactants fed through the system regardless of what form they actually exist in the reaction zone. The optimum feed rate varies directly with the temperature, with higher feed rates accompanying the higher temperatures. This feed rate will usually fall in the range of 0.1 to 100 volumes of condensed reactants per volume of catalyst per hour.

The most preferable feed rates are chosen to minimize the amount of unreacted starting materials without pushing the reaction to such extremes that side reactions begin to dominate. As such, the conversion of the least reactive acid is desirably 85-99 percent. A more desirable range is 90-98 percent. And the most desirable conversion of starting acids is 95-97 percent. Although the reaction will take place beyond these limits, below 85 percent conversion will give outstanding overall ketone selectivity with fewer by-products, but will require an additional, more costly distillation during product recovery to separate the unreacted starting material from the product for recycle. And conversions beyond 99 percent begin to entail significant product losses as increasing contributions by side reactions convert already formed product as well as the starting materials into side products.

Proper selection of the ratio of the starting materials can improve the overall success of the reaction. The stoichiometry of mixed ketone preparation suggests a molar ratio of 1:1 of the starting carboxylic acids to achieve the maximum amount of the mixed product while minimizing the production of the two symmetrical ketones. In reality, however, one of the starting acids might be more expendable than the other, so that by using more of the more expendable acid, the yield of asymmetrical ketone product from the less expendable acid increases.

Thus, the choice of which ratio of starting materials to use will depend on the overall objectives, the deviation of the actual catalyst from these statistical limits, and what to do with the by-products.

For this reason, the preferred ratio of starting carboxylic acids is generally in the 5:1 to 1:1 range with the material of less importance being in abundance. A more preferable range to optimize the return without co-producing large amounts of by-product is 3:1 to 1:1. And the most preferable range of starting carboxylic acids is 2:1 to 1:1. In the latter case, the selectivity to the unsymmetrical ketone is good without producing unacceptably large amounts of by-product.

It is possible to feed the carboxylic acids into the reactor with up to 50 weight percent of water. Water can prolong catalyst life by preventing coke formation on the catalyst.

When the activity and/or selectivity of the catalyst decrease due to coking, the promoted alumina-titania catalyst can be regenerated using a gas containing 0.1-100 percent oxygen at appropriate temperatures for various times, the key being how much carbon dioxide and carbon monoxide exist in the off-gases. A preferable range is 1-20 percent and a more preferable range is 3-10 percent oxygen. Any inert diluent is acceptable including nitrogen, helium, argon, neon, and water. It is possible to use carbon dioxide as the oxidant while monitoring the amount of carbon monoxide existing in the off-gases. In this case, the carbon dioxide serves as both the inert diluent and the source of oxygen. And it may be diluted with any other inert diluent. But using carbon dioxide generally requires higher regeneration temperatures.

Regeneration temperatures generally fall in the 300-700° C. range. More preferably, they exist in the 350-600° C. range. And the most preferable temperatures for catalyst regeneration are 400-500° C. Coincidentally, these are similar temperatures at which the ketonization reaction takes place, albeit in the absence of the regenerating oxidant. At the most preferable regeneration temperatures, the time required to reduce the carbon oxides to 1 percent of their highest level is generally 0.5 to 8 hours with a feed rate of 10 catalyst volumes per hour of the regenerating gas.

This treatment can remove up to several weight percent of carbon on the catalyst surface. It also restores essentially complete catalyst activity. The catalyst integrity is unaffected because of the inherent strength of the alumina-titania material and the fact that the treatment takes place at mild temperatures.

Suitable inert agents to use during the regeneration process include water, nitrogen, carbon dioxide, argon, helium, and neon. The most preferred agents are water and nitrogen solely because they are most readily available and least expensive.

As used herein, the indefinite article "a" means one or more.

Unless otherwise indicated, all numbers expressing quantities of ingredients, properties such as molecular weight, reaction conditions, and so forth used in the description and claims are to be understood as being modified in all instances by the term "about." Accordingly, unless indicated to the contrary, the numerical parameters set forth in the following description and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters describing the invention are approximations, the numerical values set forth in the specific examples are reported as precisely as possible. Any numerical value, however, inherently contains certain errors necessarily resulting from the standard deviation found in their respective testing measurements.

The invention is further illustrated and described by the following examples.

starting material. Selectivity is defined as the ratio of the number of moles of product obtained to the number of moles of the starting material reacted.

Example 1

100 g of a catalyst material containing 40 wt % titania and 60 wt % alumina were soaked in 100 ml of a 10% solution of KOH in water for 24 hrs at 60° C. under vacuum. The KOH solution was drained. The catalyst was washed three times with 100 ml of deionized water and dried at 130° C. for 4 hrs.

70 ml of the resulting catalyst were placed in a stainless steel reactor, one inch in diameter. The bottom and the top of the catalyst bed were each filled with 10 ml of glass beads. The reactor was heated inside an electric furnace. A mixture of acetic acid and isobutyric acid in a molar ratio of 1.6:1, having 10% water by weight, was introduced from the top to the bottom of the reactor through a line preheated to 170° C. at a rate of 70 ml/hr. The product was collected every 1-2 hrs in a condenser chilled to 0° C., weighed, and analyzed by GC. The results are summarized in Table 1 below.

TABLE 1

MIPK run with KOH treated titania-alumina catalyst at 1.6 molar ratio of acetic acid to isobutyric acid.

| | Isobutyric acid basis (%) | | | | Acetic acid basis (%) | | | | | Mass | GC accountability (%) | |
|---|---|---|---|---|---|---|---|---|---|---|---|---|
| Temp. (° C.) | Conversion | MIPK Yield | MIPK Selectivity | DIPK Yield | DIPK Selectivity | Conversion | MIPK Yield | MIPK Selectivity | Acetone Yield | Acetone Selectivity | Balance (%) | Organic Phase | Aqueous Phase |
| 450 | 83.0 | 67.8 | 80.8 | 12.2 | 14.5 | 99.6 | 42.3 | 42.5 | 51.6 | 51.8 | 97.1 | 98.8 | 99.1 |
| 475 | 93.0 | 66.6 | 71.3 | 16.3 | 17.5 | 100.0 | 41.6 | 41.6 | 49.1 | 49.1 | 92.6 | 97.1 | 99.3 |
| 475 | 92.5 | 65.3 | 70.6 | 15.5 | 16.8 | 100.0 | 40.8 | 40.8 | 47.9 | 47.9 | 91.1 | 97.1 | 99.2 |
| 475 | 91.2 | 69.8 | 76.6 | 16.5 | 18.2 | 100.0 | 43.6 | 43.6 | 51.9 | 51.9 | 97.4 | 97.9 | 99.1 |
| 500 | 99.5 | 64.7 | 65.0 | 18.5 | 18.6 | 100.0 | 40.4 | 40.4 | 43.3 | 43.3 | 90.5 | 94.9 | 99.6 |

EXAMPLES

Active catalyst material, titania and alumina, was obtained from commercial sources. Analyses were completed using Varian 6890+ gas chromatograph equipped with a 30 meter Quadrex 007 CW (carbowax) capillary column, 0.53 mm in diameter, and a thermal conductivity detector.

Yield is defined as the ratio of the number of moles of product obtained to the number of moles of the starting material. Conversion is defined as the ratio of the number of moles of starting material reacted to the number of moles of the Example 2 (Comparative)

Example 1 was repeated, except the catalyst contained 100% titania. The space time velocity in this example was 1.0 $hr^{-1}$. The results are summarized in Table 2 below.

TABLE 2

MIPK run with KOH treated titania catalyst at 1.6 molar ratio of acetic acid to isobutyric acid.

| | Isobutyric acid basis (%) | | | | Acetic acid basis (%) | | | | | Mass | GC accountability (%) | |
|---|---|---|---|---|---|---|---|---|---|---|---|---|
| Temp. (° C.) | Conversion | MIPK Yield | MIPK Selectivity | DIPK Yield | DIPK Selectivity | Conversion | MIPK Yield | MIPK Selectivity | Acetone Yield | Acetone Selectivity | Balance (%) | Organic Phase | Aqueous Phase |
| 475 | 96.8 | 60.0 | 61.8 | 14.8 | 34.8 | 99.6 | 37.5 | 37.6 | 12.8 | 31.7 | 84.1 | 94.2 | 100.0 |
| 475 | 94.4 | 67.2 | 70.9 | 13.2 | 29.7 | 99.4 | 42.0 | 42.2 | 15.7 | 46.6 | 89.2 | 97.4 | 99.9 |
| 475 | 93.4 | 65.4 | 69.7 | 12.0 | 28.5 | 99.3 | 40.9 | 41.2 | 15.1 | 40.7 | 86.3 | 97.1 | 100.0 |
| 475 | 98.7 | 63.8 | 64.5 | 18.8 | 40.6 | 99.6 | 39.8 | 40.0 | 12.2 | 32.4 | 76.2 | 95.8 | 99.6 |

As seen from Tables 1 and 2 above, when the catalyst was composed of 60% by weight of alumina and 40% by weight of titania, in its anatase form, the catalyst lifetime increased almost twice, compared to the pure titania, in its anatase form. The yield of MIPK has not decreased (in some cases, it even slightly increased). Both catalysts were treated with a Group 1 metal hydroxide, according to the same procedure in U.S. Pat. No. 4,950,763. Therefore, the improvement in the catalyst must be attributed to the presence of aluminum oxide.

Since aluminum oxide is cheaper than titanium oxide, a cheaper catalyst having a longer life may be achieved.

The invention has been described in detail with particular reference to preferred embodiments thereof, but it will be understood that variations and modifications can be effected within the spirit and scope of the invention.

We claim:

1. A catalyst for preparing ketones from carboxylic acids, comprising a mixture of titanium dioxide and at least 50% by weight of aluminum oxide, and a catalyst promoter comprising a Group 1 or 2 metal hydroxide, or a salt thereof.

2. The catalyst according to the claim 1, which comprises up to 50% by weight of titanium dioxide.

3. The catalyst according to claim 1, which comprises about 40% by weight of titanium dioxide.

4. The catalyst according to claim 1, which comprises about 60% by weight of aluminum oxide.

5. The catalyst according to claim 1, wherein the Group 1 or 2 metal hydroxide is KOH.

6. The catalyst according to claim 1, which comprises 0.5-10 weight percent of the catalyst promoter.

7. The catalyst according to claim 1, which comprises 0.5-5 weight percent of the catalyst promoter.

* * * * *